(12) United States Patent
Pintor Just et al.

(10) Patent No.: US 10,933,100 B2
(45) Date of Patent: Mar. 2, 2021

(54) **PREPARATION AND USE OF AN EXTRACT OF *ARTEMIA SALINA* TO TREAT THE OCULAR SURFACE**

(71) Applicant: Ocupharm Diagnostics, S.L., Madrid (ES)

(72) Inventors: Jesús Jerónimo Pintor Just, Madrid (ES); María Jesús Pérez De Lara, Madrid (ES); Fernando Huete Toral, Madrid (ES); Basilio Colligris, Madrid (ES); Juan Gonzalo Carracedo Rodríguez, Madrid (ES)

(73) Assignee: Ocupharm Diagnostics, S.L., Madrid (ES)

( * ) Notice: Subject to any disclaimer, the term of this patent is extended or adjusted under 35 U.S.C. 154(b) by 69 days.

(21) Appl. No.: 16/318,987

(22) PCT Filed: Jul. 14, 2017

(86) PCT No.: PCT/ES2017/000092
§ 371 (c)(1),
(2) Date: Jan. 18, 2019

(87) PCT Pub. No.: WO2018/015582
PCT Pub. Date: Jan. 25, 2018

(65) Prior Publication Data
US 2019/0275089 A1    Sep. 12, 2019

(30) Foreign Application Priority Data
Jul. 20, 2016 (ES) .................................. 201600607

(51) Int. Cl.
*A61K 35/612* (2015.01)
*A61K 35/63* (2015.01)
(Continued)

(52) U.S. Cl.
CPC ............ *A61K 35/63* (2015.01); *A61K 9/0048* (2013.01); *A61K 9/127* (2013.01); *A61K 35/612* (2013.01); *A61P 27/02* (2018.01); *A61P 27/04* (2018.01)

(58) Field of Classification Search
CPC .................................................... A61K 35/612
See application file for complete search history.

(56) References Cited

U.S. PATENT DOCUMENTS

2013/0011469 A1   1/2013   Minatelli et al.

FOREIGN PATENT DOCUMENTS

| AL | WO2010/106571 A2 | 9/2010 |
| WO | WO2015/169728 A1 | 11/2015 |

OTHER PUBLICATIONS

Google Patents English translation of Cho et al., KR 20020073725 A, 2002. (Year: 2002).*

(Continued)

*Primary Examiner* — Rosanne Kosson
(74) *Attorney, Agent, or Firm* — Cook Alex Ltd.

(57) ABSTRACT

The present invention relates to the preparation of an extract of the crustacean *Artemia salina* and to the use thereof to treat diseases of the ocular surface. The invention describes the application of the extract mainly by means of soaps, eyedrops, eye solutions, eye washes, aerosols, in the presence of unguents, creams, gels or contact lenses, inter alia. The application of the *Artemia salina* extract is efficient for treating pathologies consistent with ocular dryness (dry eye) and the manifestations thereof such as the appearance of injuries or ulcers on the ocular surface or infections caused by microorganisms and associated with dry eye, also on of the ocular surface.

6 Claims, 1 Drawing Sheet

(51) Int. Cl.
*A61P 27/04* (2006.01)
*A61K 9/00* (2006.01)
*A61K 9/127* (2006.01)
*A61P 27/02* (2006.01)

(56) References Cited

OTHER PUBLICATIONS

International Search Report (with English translation), counterpart PCT Appl. No. PCT/ES2017/000092, dated Oct. 3, 2017.

* cited by examiner

PREPARATION AND USE OF AN EXTRACT OF *ARTEMIA SALINA* TO TREAT THE OCULAR SURFACE

FIELD OF THE INVENTION

The present invention relates to the acquisition and application of extracts obtained from the cysts, nauplii or adults of the organism *Artemia salina*, that are isolated and mixed in different proportions, either alone or in combination with other products, natural or synthetic extracts for the preparation of pharmaceutical compositions, particularly for ocular use. These compositions shall be mainly made in the form of soaps, eyedrops, eye solutions, eye washes, aerosols, in the presence of unguents, creams, gels or contact lenses, for treating pathologies of the ocular surface.

STATE OF THE ART

There are various problems that patients may have on their ocular surface. The most prevalent being dry eye, which may arise in many cases as a consequence of superficial corneal injuries, and infections of the ocular surface (Thoft R A. (1985). Relationship of the dry eye to primary ocular surface disease. Trans Ophthalmol Soc U K. 104 (Pt 4):452-7).

Dry eye is defined as a multifactorial disease of the tear and of the ocular surface which causes symptoms of discomfort, visual problems and instability of the tear film, with a potential damage to the ocular surface and increase in the risk of infections. (Al-Saedi Z, Zimmerman A, Bachu R D, Dey S, Shah Z, Baugh R, Boddu S H (2016). Dry Eye Disease: Present Challenges in the Management and Future Trends. Curr Pharm Des. June 2013. [Epub ahead of print]).

It is accompanied by an increase in osmolarity of the tear film and an inflammation of the ocular surface.

In the case of Caucasian populations (white race), the normal osmolarity ranges from 319 to 314 mOs (Potvin R, Makari S, Rapuano C J. (2015). Tear film osmolarity and dry eye disease: a review of the literature. Clin Ophthalmol. 9:2039-2047). Although there is no strict limit, it is considered that 314 mOs is the lower limit of normality and all measurements that are below that value are labelled as "poor quality of the tear film" and also as "suspicion of dry eye".

Normal tear volume quantity ranges from 10 to 15 mm in Schirmer's test strips. Although there is no strict limit, it is considered that 5.5 mm is the lower limit of normality and all measurements that are below that value are labelled as "poor quality of the tear film" and also as "suspicion of dry eye".

Dry eye is a highly prevalent disease affecting between 14 and 33% of the worlds population, depending on the study and definition used. Some diseases of the eye surface are manifested with ocular dryness, such as Sjögren's syndrome or aniridia. However, ocular dryness and its consequences are also manifested in systemic diseases such as rheumatoid arthritis, lupus or sarcoidosis. Likewise, ocular dryness and its consequences may arise due to environmental situations such as, for example, conditions of very low humidity, high temperatures, heating devices or air conditioners or the use of electronic devices such as computers, mobile phones or tablets. Furthermore, it is important to recall that some pharmaceutical and/or surgical treatments may entail ocular dryness, such as the use of decongestants and antihistamines, tranquilizers, antidepressants and sleeping pills, diuretics, contraceptive pills, some anaesthetics, drugs for treating arterial hypertension (beta blockers) and for digestive disorders (anticholinergics) or refractive surgery operations (Scot E Moss, Ronald Klein, Barbara E K Klein. (2000). Prevalence of and Risk Factors for Dry Eye Syndrome. Arch Ophthalmol. 118:1264-1268)

The classification of dry eye is based on two blocks: from an etiological perspective and from the influence of the environment, which predisposes to the development of dry eye.

The etiological classification is in turn subdivided into two main groups: Dry eye due to deficiency in the aqueous phase of tears and evaporative dry eye. However, these groups are not independent, given that the disease started in one of the main groups may coexist with circumstances that cause dry eye within the other group.

The current treatment options for dry eye are tear supplements, also called lubricants, known as artificial tears (Marshall L L, Roach J M (2016). Treatment of Dry Eye Disease. Consult Pharm. 31(2): 96-106). The effectiveness of this option is difficult to verify, as its effects may not be observed or because the currently available agents do not have a discernible activity of the lubrication effect. An improvement may be observed in the symptoms, but it is not sufficient to resolve the pathology on the ocular surface or the inflammation presented on the ocular surface.

Other treatment options are anti-inflammatory drugs such as cyclosporine, corticoids, tetracyclines and analogues; tear retention devices, such as permanent occlusion plugs of the tear duct; moisture glasses; contact lenses; and self-transplant of the tear gland. However, none of these treatments are free from undesired secondary effects.

Corneal and conjunctival injuries occur as a very typical consequence of ocular dryness, since as there are no tears or the existent tears have a very poor quality, the friction of the eyelids causes the injury or ulcer (Liu C Y, Kao W W (2015). Corneal Epithelial Wound Healing. Prog Mol Biol Transi Sci 134:61-71).

The therapeutic approaches are practically non-existent and in general are focussed on the application of antibiotic ointments with the aim of avoiding opportunistic infections that may occur, leaving the healing process to resolve itself (Ljubimov A V, Saghizadeh M. (2015). Progress in corneal wound healing. Prog Retin Eye Res. 49:17-45).

Infections of the ocular surface as a consequence of dry eye are the result of a defective tear film which favours the establishment of the pathogenic microorganisms (Narayanan S, Redfern R L, Miller W L, Nichols K K, McDermott A M (2013) Dry eye disease and microbial keratitis: is there a connection? Ocul Surf. 11 (2):75-92). In most cases, it relates to bacteria, fungi and virus. In some cases, the infections only affect part of the eye, whether the conjunctiva or the cornea, but, generally, both are affected, since ocular dryness affects the entire ocular surface exposed to air. Even sometimes, when the infection is severe, it may pass to the inside of the eye, and it is then very difficult to treat.

The eye, in healthy conditions, has two defence mechanisms to defend itself from opportunistic infections, the tear film and the corneal epithelium. The tear is a structured and specialized humid film, which covers the conjunctiva and the cornea. Its composition, from a quantitative and qualitative standpoint, must be kept stable to achieve an adequate eye health and good visual function. It is for this reason that a deficiency thereof, as occurs in dry eye, is one of the most important factors as a cause of infections (D V Seal, J I McGill, I A Mackie, G M Liakos, P Jacobs and N J Goulding (1986). Bacteriology and tear protein profiles of the dry eye. Br J Ophthalmol; 70:122-125).

From the standpoint of infections, the tear film is the first line of ocular defence since it contains dissolved substances with bactericide and bacteriostatic capacity. Lysozyme and lactoferrin are the main components of tears, the first being attributed to bactericide activity and the second to bacteriostatic activity.

If the tear is altered by a physical or chemical process or by a pathological state, the bactericide activity may be decreased or insufficient and therefore the eye will be inclined to have infections.

Drugs from different families are used for treating infections, among which we have as bactericide agents: aminoglycosides, penicillins, cephalosporins, quinolones and as bacteriostatic agents: erythromycin, tetracycline, chloramphenicol and the sulfonamides, and substances of new creation (the following patents serve as an example: WO3015752, U.S. Pat. No. 6,569,443, WO0119366, WO02083178); in addition to antiviral and antifungal agents.

Some of these drugs cause secondary effects on an ocular and systemic level. Among the adverse reactions found on an ocular level the incidence of allergies, allergic blepharitis, precipitates in the front part of the cornea, white corneal plaques in patients with keratoconjunctivitis sicca has been described, in addition to the undesired effect they cause on the healing of corneal injuries (Crews, S J (1977) Ocular adverse reactions to drugs. Practitioner 219: 72; Fraunfelder, F T (1989) Drug induced ocular side effects and drug interactions 3$^{rd}$ Edition. Lea and Febiger, Philadelphia; Ball, A P, Geddes, A M, Davey, P G, Farrell, I D and Brookes, G R (1980) Clavulanic acid and Amoxycillin: a clinical, bacteriological and pharmacological study. Lancet 1 :620-623)

*Artemia salina* is a branchiopod crustacean of the Anostraca order typical of continental salt waters, very widely distributed throughout the world. Its composition has mainly fatty acids (Hachem Ben Naceur, Gabila ghazali, Amel Ben Rejeb Jenhani and Mohamed Salah Romdhane. Study of the fatty acid composition of *Artemia salina* cysts from Tunisia. Journal of the Marine Biological Association of the United Kingdom, 2013, 93(7), 1795-1803.), proteins (Claus C, Benijts F, and Vandeputte. The biochemical composition of the larvae of two strains of *Artemia salina* (L.) reared on two different algal food. J. Exp. Mar. Biol. Ecol. 1979; 36, 171-183), amino acids (Landau M, Miyamoto G, Bolis C. Growth and amino acid composition of *Artemia salina* (L, 1758) fed algae grown in different media (Anostraca). Crustaceana, 1984, 49 (1), 318-321), components of nucleotide nature with guanine (Warner A H, McClean D K. Studies on the Biosynthesis and Role of Diguanosine Tetraphosphate during Growth and Development of *Artemia salina*. Devel. Biol. 1968, 18, 278-293), D-myo-inositol-1, 4,5-triphosphate and glycans (Gallagher M, Brown W D. Composition of San Francisco bay brine shrimp {*Artemia salina*). J Agrie Food Chem. 1975; 23(4):630-642).

The study on a possible cosmetic use of a preparation of the crustacean *Artemia salina* is reflected in several patents (WO/1999/038483A1, WO/1999/038483A8, EP1049455A1, WO/2015/107286A2, WO/2015/107286A3, EP1049455B1) wherein an enzymatic extract is claimed, produced by a method and with claims of totally different use to those disclosed in the present invention.

On the composition there are interesting elements that give the extract of *Artemia salina* interesting properties such as ultraviolet light absorption by the nucleotides (Pintor J. Commentary: Why are such high concentrations of nucleotides in the lens? *Purinergic signalling.* 2011; 7(2):169-170), the role of inositol as second intracellular messenger in some cells and tissues, fatty acids as lubricants and, finally, the glycans, which represent a source of energy for cells due to their carbohydrate composition but they are also important to maintain correct bacterial flora in the mucus membranes and have a great hydration capacity due to their high number of hydroxyl groups (Varki A, Cummings R D, Esko J D, Stanley P, Hart G, Aebi M, Darvill A, Kinoshita T, Packer N H, Prestegard J J, Schnaar R L, Seeberger P H, editors. Essentials of Glycobiology [Internet]. 3rd edition. Cold Spring Harbor (NY): Cold Spring Harbor Laboratory Press; 2015; Van den Steen P, Rudd P M, Dwek R A, Opdenakker G. Concepts and principles of O-linked glycosylation, Crit Rev Biochem Mol Biol. 1998; 33(3): 151-208. Hang H C, Bertozzi C R. The chemistry and biology of mucin-type O-linked glycosylation. Bioorg Med Chem. 2005; 13(17): 5021-5034).

EXPLANATION OF THE INVENTION

The present invention relates to the acquisition and application of extracts obtained from the cysts, nauplii or adults of the organism *Artemia salina*, that are isolated and mixed in different proportions, either alone or in combination with other products, natural or synthetic extracts for the preparation of pharmaceutical compositions particularly for ocular use.

An "extract of *Artemia salina*" is understood to be a combination of compounds extracted from the crustacean *Artemia salina* by means of a chemical, biochemical or biological extraction (e.g. by means of water or chemical solvents). The extract may include any of the various proteins, carbohydrates, nutrients, secretion products and similar derived from *Artemia salina*.

The present invention discloses the manner of obtaining the extracts of *Artemia salina*, and the applications thereof in aspects such as tear volume, the rate of healing of injuries on the eye surface and the maintenance of a compensated biota of the ocular surface.

The compositions can be made in a wide variety of types of products that include, but are not limited to: eyedrops, drops, lotions, creams, gels, bars, sprays, unguents, washes, cleaning liquids, shampoos, foams, wipes, patches, hydrogels and films. These types of products may contain several types of acceptable topical vehicles including, but not limited to: solutions, suspensions, emulsions such as microemulsions and nanoemulsions, gels, solids and liposomes. The following are non-limitative examples of said vehicles.

The useful topical compositions in the present invention can be formulated as solutions. Although it is preferred that the solution is aqueous, in certain cases, the composition may, in addition to, or instead of water, include acceptable organic solvents. Examples of suitable organic solvents include: propylene glycol, polyethylene glycol (200-600), polypropylene glycol (425-2025), glycerol, 1,2,4-butanetriol, sorbitol esters, 1,2,6-hexanetriol, ethanol and mixtures thereof in addition to others. One or more solvents may be present from proportions of approximately 50% to 99.99% or from approximately 90% to 99% of an acceptable aqueous or organic solvent.

Although it is preferred that the topical composition of the present invention includes water, the topical compositions may be, alternatively, compositions or unguents that include organic solvents and/or of silicone, oils, lipids and anhydrous waxes. An unguent may contain a simple base of animal or vegetable oils or semisolid hydrocarbons. An unguent may contain from approximately 2% to 10% of an emollient or emollients plus 0.1% to 2% of a thickening agent or agents. Examples of thickening agents include, but are not limited to, those stated in the ICI Handbook 2979-84.

The useful topical compositions in the present invention may be formulated as emulsions. The emulsifiers may be ionic, anionic or cationic. Examples of emulsifiers include but are not limited to those stated in the ICI Handbook, pp. 2962-71.

Other useful materials may also be present in the compositions in the present invention. These include wetting agents, viscosifying agents, pH adjusters, minerals and preservatives. Examples of said agents are listed in pp. 2922-23, 2926-28, and 2892 of the ICI Handbook.

EXAMPLES

Acquisition of the Extracts of *Artemia salina*

The extracts were obtained from the cysts of *Artemia salina*, or their nauplii or from mature individuals, weighing quantities ranging from 1 mg to grams.

Extraction A): As an example of extraction A, 20 mg of cysts, nauplii or mature individuals of *Artemia salina* are taken and they are mixed with 1 ml of ultrapure water (final concentration 20 mg/mL). This preparation is mechanically homogenized for 30 seconds, twice consecutively. The result of the homogenization, and with the object of eliminating the proteins, is placed in an Eppendorf tube in a dry bath at 98° C. for two minutes. Then, it is incubated in an ice bath for 5 min. To separate the denaturalized proteins, the samples are centrifuged at 22,000×g for 4 minutes at 4° C. The supernatant resulting from the centrifugation is taken and filtered in a sterile hood by means of a 0.22µ filter. This "Extract A" is assayed in the examples that follow below.

Extraction B) As example of extraction B 20 mg of *Artemia salina* cysts are taken and they are mixed with 1 ml of a 0.9% sodium chloride solution (20 mg/mL). This preparation is mechanically homogenized for 30 seconds twice consecutively. The result of the homogenization, and with the object of eliminating the proteins, is placed in an Eppendorf tube in a dry bath at 98° C. for two minutes. Then, it is incubated in an ice bath for 5 min. To separate the denaturalized proteins, the samples are centrifuged at 22,000×g for 4 minutes at 4° C. The supernatant resulting from the centrifugation is taken and filtered in a sterile hood by means of a 0.22µ filter. This "Extract B" is assayed in the examples that follow below.

Effect of the Extracts of *Artemia salina* on Tear Levels

To perform the tear production studies, one aliquot of 10 µL of "Extract A" was taken and it was topically applied on the ocular surface of albino rabbits of New Zealand breed. The tear volume was measured after instillation of "Extract A" for a maximum time of 170 minutes. To do this, a Schirmer test was performed which consisted of placing a strip of graduated filter paper in the lower eyelid of the experimentation animal (Cho P, Yap M. Schirmer test. I. A review. Optom Vis Sci. 1993; 70(2): 152-156). During said period, it could be verified that the tear volume remained high for around 90 min to then return to its initial levels (FIG. 1). When the same protocol was performed with "Extract B", a similar profile was observed except that in the case of the latter, the increase in tear level was greater than in the case of "Extract A" (FIG. 1).

The control experiment was performed by administering 10 µL of 0.9% saline solution, wherein no changes are observed in tear volume.

Effect of the Extracts of *Artemia salina* on Corneal Healing

To mimic the corneal injuries produced by ocular dryness, extracts A and B were tested on superficial injuries made according to the described protocol (Cintran, C, Hassinger L, Kublin C L, Friend J A simple method for the removal of rabbit corneal epithelium utilizing n-heptanol. Ophthalmic Res. 1979; 11, 90-96.), wherein, after anaesthetizing the New Zealand breed rabbits, an injury has been made placing a circular filter paper soaked in n-heptanol on the animal's cornea. The healing rate is measured by quantifying the decrease in diameter of the disc against the time either with the control (0.9% saline solution), "Extract A" or "Extract B". The applications of the control or of the extract were performed by adding 10 µL of each one of them with repetitions thereof with an application interval of no more than 6 hours (FIG. 2).

The control experiment with 0.9% saline solution had an estimated healing time (time it takes to close the injury) of approximately 42 h, compared with the 26 h it took in the case of "Extract A" and 19 h that "Extract B" took.

Effect of the Extracts of *Artemia salina* on the Biota of the Ocular Surface To verify the effect of these extracts, 5 µL of tears were collected twice before applying the invention (basal levels of antimicrobial activity on the animal's surface). This volume of tears collected was applied on a filter paper disc (Whatman no. 1) and it was deposited on a petri dish whereon the bacterium *Micrococcus lisodeikticus* had previously been inoculated. This bacterium is commonly used to determine the lysozyme/lactoferrin levels in biological systems (van Bijsterveld, O. P., Arch Ophthalmol. 91, 432-434, 1974). This method is used to compare the conditions in the absence of any substance or extract, measuring the bacterial growth inhibition halo, and comparing the mm of inhibition with those obtained for the extracts.

10 µL of "Extract A" are applied on the ocular surface of New Zealand rabbits. Then, 5 µL of tears were taken at one-hour intervals for the 5 hours following the application of "Extract A". In FIG. 3, it is possible to observe the effect this extract has on the bacteria.

10 µL of "Extract B" are applied on the ocular surface of New Zealand rabbits. Then, 5 µL of tears were taken at one-hour intervals for the 5 hours following the application of "Extract B".

BRIEF DESCRIPTION OF THE FIGURES

A series of figures are attached to facilitate the understanding of the invention and forming part of this specification.

Figure 1:
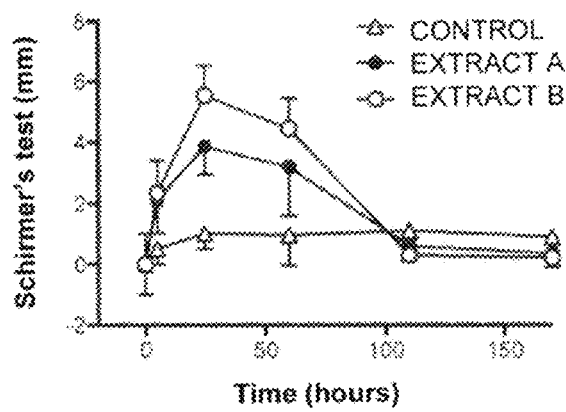
FIG. 1 represents the increase in tear volume measured with Schirmer's test when they are applied a 0.9% NaCl solution (control) and extracts A and B during 170 min. Extracts A and B retain a tear volume greater than the control.
Figure 2:
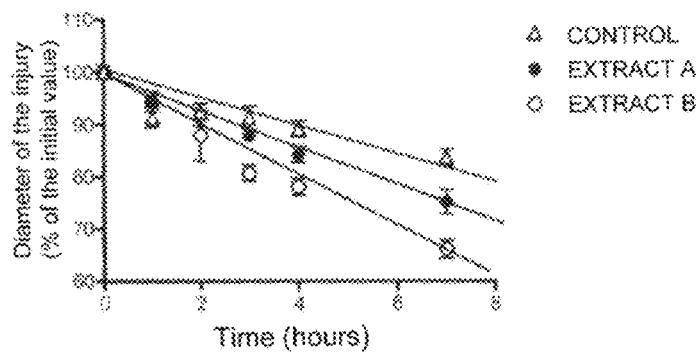
FIG. 2 shows the decrease in diameter of the injury over time for the control solution (0.9% NaCl solution), and for extracts A and B. It can be observed that, due to the gradient of the lines, it is extract B that favours a healing rate slightly greater than extract A.
Figure 3:
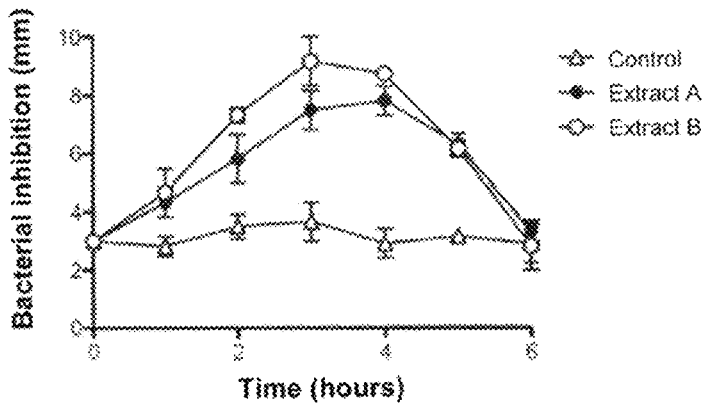
FIG. 3 shows the behaviour of the control and of extracts A and B on microorganisms, wherein it is possible to see that the extracts are more effective than the control (0.9% NaCl solution) limiting the development of microorganisms.

The invention claimed is:

1. A method for treating an eye of a subject to increase tear secretion, comprising:
   a) providing a composition comprising an extract of *Artemia salina* in an acceptable pharmaceutical vehicle therefor; and
   b) administering the composition to the eye in an effective therapeutic quantity by a topical route.

2. A method for the treatment of dry eye in an eye of a subject, wherein the subject with dry eye presents with a corneal injury and/or bacterial infection, comprising:
   a) providing a composition comprising an extract of *Artemia salina* in an acceptable pharmaceutical vehicle therefor; and
   b) administering the composition to the eye in an effective therapeutic quantity by a topical route.

3. The method of claim 1, wherein the composition has a pharmaceutical form selected from the group consisting of eyedrops, liquid drops, a liquid wash, contact lenses, a gel, a cream, an unguent, a ointment and a spray.

4. The method of claim 1, wherein the pharmaceutical vehicle comprises liposomes.

5. The method of claim 2, wherein the composition has a pharmaceutical form selected from the group consisting of eyedrops, liquid drops, a liquid wash, contact lenses, a gel, a cream, an unguent, an ointment and a spray.

6. The method of claim 2, wherein the pharmaceutical vehicle comprises liposomes.

* * * * *